United States Patent [19]

Lindman et al.

[11] Patent Number: 5,219,926
[45] Date of Patent: Jun. 15, 1993

[54] METHOD OF COVALENTLY BONDING BIOPOLYMER TO A SOLID HYDROPHILIC ORGANIC POLYMER

[75] Inventors: Bjorn Lindman; Martin Malmsten, both of Lund; Krister Holmberg, Molndal; Carina Andren, VaFrolunda, all of Sweden

[73] Assignee: Berol Nobel AB, Stenungsund, Sweden

[21] Appl. No.: 759,284

[22] Filed: Sep. 13, 1991

Related U.S. Application Data

[63] Continuation-in-part of Ser. No. 743,281, Aug. 12, 1991.

[30] Foreign Application Priority Data

Dec. 29, 1989 [SE] Sweden .............................. 8904397

[51] Int. Cl.$^5$ .................... C07K 17/08; C07K 3/00; C07K 13/00; C12N 11/08; C12N 11/02; C12N 11/06; C12N 11/04; C12Q 1/00
[52] U.S. Cl. .................... 525/54.1; 525/54.2; 525/54.21; 525/54.23; 525/54.3; 525/54.31; 530/403; 530/404; 530/405; 530/413; 530/417; 530/811; 530/812; 530/813; 530/814; 530/815; 530/816; 435/7.1; 435/7.4; 435/7.6; 435/177; 435/178; 435/179; 435/180; 435/181; 436/528; 436/529; 436/530; 436/531; 436/532; 436/533; 436/821; 436/823

[58] Field of Search .............. 525/54.1, 54.2, 54.21, 525/54.22, 54.23, 54.3, 54.31; 530/403, 404, 405, 412, 413, 417, 811, 812, 813, 814, 815, 816; 435/4, 7.1, 7.2, 7.4, 7.6, 177, 178, 179, 180, 181; 436/528, 529, 530, 531, 532, 533, 821, 823

[56] References Cited

U.S. PATENT DOCUMENTS

| 4,188,263 | 2/1980 | Hulsmann et al. | 435/179 |
| 4,450,231 | 5/1984 | Ozkan | 436/506 |

OTHER PUBLICATIONS

Muzzarelli "Natural Chelating Polymers", Pergamon Press, Oxford, 1973, pp. ix–xii.
Webster's Ninth New Collegiate Dictionary, 1986, p. 152.

*Primary Examiner*—Nathan M. Nutter

[57] ABSTRACT

A process for covalently bonding biopolymer, such as protein, to an organic polymer surface coated with hydrophilic nonionic polymer having groups reactive with the biopolymer and having a cloud point in the reaction medium that is at least 5° C. above the temperature at which the coated organic polymer surface is to be used, which comprises reacting biopolymer with the surface in an aqueous reaction medium, at a temperature not less than 5° C. below the cloud point; but not above a temperature at which the biopolymer is deleteriously affected, and preferably not above about 100° C., the product comprises a biopolymer immobilized on a hydrophilic solid surface having a nonionic polymer and a hydrophilic layer, coupled thereto via biopolymer-reactive groups of the nonionic polymer, and accordingly has low spontaneous adsorption of proteins and other biopolymers through electrostatic attraction and/or hydrophobic interaction.

10 Claims, No Drawings

METHOD OF COVALENTLY BONDING BIOPOLYMER TO A SOLID HYDROPHILIC ORGANIC POLYMER

This application is a continuation-in-part of Ser. No. 743,281, filed Aug. 12, 1991.

The immobilization of proteins and other biopolymers to solid surfaces is an established technique for a number of biochemical applciations, such as solid phase diagnostics, analysis with biosensors, affinity chromatography, extra-corporeal therapy, and bio-organic synthesis. In all of these cases, the biopolymer is bonded to a solid surface, and its biological activity then utilized for a specific purpose, such as in solid phase diagnostics, extracorporeal therapy, biological synthesis, and treatment of implants.

In solid phase diagnostics, an antibody is frequently immobilized on a plastic surface, usually of polystyrene. When in contact with a body fluid, the immobilized antibody bonds any antigen that may be present. The antibody-antigen complex is then detected by means of a labelled antibody. The labelling may be in the form of a radioactive isotope, a floroescent group, or an enzyme conjugate.

In extracorporeal therapy, a biologically-active substance is bonded to a chamber through which the patient's blood is conducted. A current example of extracorporeal therapy is hemoperfusion across an immobilized immunostimulating substance. Interferons and interleukins are examples of such substances. Examples of diseases that can be treated by this technique are cancer and AIDS.

In bio-organic synthesis, use is made of enzymes for producing organic compounds. An appropriate use for bio-organic synthesis is lipid transformations, i.e. transforming a lipid, usually a triglyceride, into another lipid. Most enzymes are expensive, and frequent reuse is necessary to ensure good process economy. Consequently, the use of immobilized enzymes is of interest in most large-scale enzymatic processes.

In the treatment of implants, a biopolymer is bonded to the surface which comes into contact with biological tissue. The biopolymer, for example collagen, promotes tissue growth and stiumulates cell colonization on the implant, resulting in an increased biocompatibility. This technique can be utilized also for in vitro treatment of cell culture dishes to improve cell adhesion.

The immobilization of proteins on both organic and inorganic surfaces is today a well-established technique (see Chapter 4, *Principles of Immobilization of Enzymes, Handbook of Enzyme Biotechnology*, Second Edition, Ellis Horwood Limited, 1985), and it is possible to bond a large amount of protein to the surface while retaining adequate biological activity.

However, it has been found that most solid surfaces are so constituted that they adsorb proteins and other biopolymers spontaneously. Such adsorption from aqueous solution is promoted primarily by two types of physical forces, electrostatic attraction, and hydrophobic interaction. Most surfaces at normal pH are negatively charged, but usually they also contain hydrophobic domains. A protein usually has positive, negative and hydrophobic seats, which means that a protein is attracted to most surfaces, on the one hand by electrostatic attraction between positive seats and negatively charged groups in the surface, and, on the other hand, by hydrophobic interaction between hydrophobic domains of the protein and the surface. This is described in, for example, *Surface and Interfacial Aspects of Biomedical Polymers*, Ed. J. D. Andrade, Plenum Press (1985), Vol. 2, p. 81.

Such nonspecific adsorption by electrostatic attraction and hydrophobic interaction is an undesired phenomenon for the abovementioned applications. In solid phase diagnostics, it results in an impaired sensitivity and a shorter life of the diagnostic kit. In both extracorporeal therapy and in bio-organic synthesis, spontaneous adsorption causes impaired activity and a shorter product life.

One way of drastically reducing the adsorption proteins and other biopolymers on solid surfaces is to provide the surfaces with a layer of an uncharged hydrophilic polymer. One example of a polymer that has been used for this purpose is polyethylene glycol (see C. G. Golander, *Preparation and Properties of Functionalized Polymer Surfaces*, Dissertation, Royal Institute of Technology, Stockholm (1986), but other substances, such as polysaccharides, for example dextran, cellulose ethers and starch; polyvinyl alcohol; and neutral silica sol have also been used for this purpose.

By coating the surface with a layer of uncharged hydrophilic polymer, such as polyethylene glycol side chains or "tails", both electrostatic attraction and hydrophobic interaction can be avoided.

One way of attaching polyethylene glycol tails to a solid polymer surface is first, to subject the surface to so-called acidic etching, then to adsorb a cationic polymer, such as polyethylene imine, to the surface, and finally, to react a reactive polyethylene glycol derivative with available amino groups in the polyethylene imine layer. This technique has been described in *Prog. Colloid Polym. Sci.* 74 113–119 (1987). During the acidic etching (which is carried out with potassium permanganate in concentrated sulphuric acid), carboxylic acid and sulphonic acid groups as well as sulphuric acid esters are formed on the surface, forming a highly negatively charged polymer surface, to which the cationic polyethylene imine is bonded very strongly by electrostatic forces. Furthermore, it is likely that upon drying salt bonds between imino groups in the polyethylene imine and carboxylate and sulphonate groups on the surface gradually are transformed into amide or imide bonds, which gives an even stronger bond of the polyethylene imide to the surface.

Even though hydrophilized surfaces made by this technique, described in the above paper, give an improved repellency of biopolymers, adsorption by electrostatic attraction and hydrophobic interaction is still much too high for a number of applications.

Hydrophilic surfaces of this type are of great interest in, inter alia, the above-mentioned applications of immobilized proteins. To covalently bond protein to such a surface, it is necessary to introduce into the hydrophilic layer reactive functional groups serving as anchoring points for the protein. However, it has proved extremely difficult to covalently bond protein to thoroughly hydrophilic surfaces, even if the surfaces contain a high concentration of reactive groups.

The hydrophilic surface does not attract the protein. On the contrary, it acts as a repellent, because it is energetically unfavorable for a protein in aqueous solution to approach such a surface. As a result, the amount of immobilized protein usually will be low, regardless of whether it is an antibody for solid phase diagnostics, an immuno-stimulating substance for extracorporeal therapy, or an enzyme for bio-organic synthesis. Thus, it is difficult to both adsorb and covalently bond proteins from an aqueous solution to hydrophobic polymer surfaces coated with a thoroughly covering layer of a hydrophilic uncharged polymer, for example polyethylene glycol or a polysaccharide.

In accordance with the present invention, large amounts of biopolymer, such as protein, are immobilised on a hydrophilic surface. The resulting immobilised biopolymer hydrophilic surface has a low spontaneous adsorption of undesired products. The invention provides a process for covalently bonding biopolymer, such as protein, to an organic polymer surface coated with hydrophilic nonionic polymer having groups reactive with the biopolymer and having a cloud point in the reaction medium that is at least 5° C. above the temperature at which the coated organic polymer surface is to be used, which comprises reacting biopolymer with the surface in an aqueous reaction medium, at a temperature not less than about 5° C. below the cloud point; but not exceeding a temperature at which the biopolymer is deleteriously affected, preferably not above about 100° C., and still more preferably within the range from about 30° to about 50° C. The product comprises a biopolymer immobilised on a hydrophilic solid surface having a hydrophilic nonionic polymer layer, coupled thereto via biopolymer-reactive groups of the nonionic polymer, and accordingly has low spontaneous adsorption of proteins and other biopolymers through electrostatic attraction and/or hydrophobic interaction.

The basic principle of the invention utilises the unusual dependence on temperature of the cloud point exhibited by nonionic water-soluble polymers. For example, polyalkylene glycols and nonionic cellulose alkyl, hydroxyalkyl and benzyl ethers exhibit a solubility in water that decreases at elevated temperatures. The mechanism behind this decrease with increasing temperature has still not been fully explained, but it is thought that the spatial arrangement of the alkylene oxide groups is changed as temperature increases, making the alkylene oxide groups increasingly hydrophobic, and thus less soluble in water. As temperature increases, the water solubility of the polymer becomes so low that the solution separates into two phases. The temperature at which phase separation occurs is usually termed the cloud point of the solution. Polyalkylene glycols and cellulose alkyl, hydroxyalkyl and benzyl ethers have definite cloud points, and those especially useful in the invention and therefore preferred have cloud points within the range from about 10° to about 100° C., preferably from 30° to 50° C.

The nonionic hydrophilic polymer is hydrophilic at the temperature at which the biopolymer coated surface is used, and has a cloud point that is at least 5° C. above and preferably at least 10° C. above the temperature at which the coated surface is used. A preferred protein immobilisation temperature is from 3° C. below the cloud point or flocculation temperature of the nonionic hydrophillic polymer in the reaction medium, up to a temperature of about 50° C.

It is thus apparent that the reaction proceeds at a temperature from 5° C. below the cloud point of the nonionic hydrophilic polymer in the reaction medium up to 100° C. or higher (thus diminishing or further inhibiting any tendency of the hydrophilic nonionic polymer on the organic polymer surface to dissolve in the reaction medium) at the interface between nonionic polymer on the surface and the biopolymer in solution in the reaction medium. Exactly what takes place at the interface during the reaction is not known. As the biopolymer reacts with nonionic polymer on the surface, biopolymer is removed from the reaction medium, and immobilized on the surface.

The concentration of biopolymer in the reaction medium can vary within any desired limits but is normally not in excess of the amount which is soluble therein. Usually, the concentration is within the range from about 0.001 and about 10% by weight of the reaction medium.

The pH of the reaction medium should be within the range from about 4 to about 9. pH can be adjusted if required by addition of conventional buffer salts controlling the pH range.

The reaction is allowed to proceed at the selected reaction temperature until the desired amount of biopolymer has become immobilized on the polymer surface. In most cases this amount will be within the range from about 0.1 to about 100 mg per square meter of surface. This usually takes from about 10 minutes to about 48 hours, but the time is in no way critical, and depends on the type of polymer on the surface and the type of biopolymer.

As indicated above, the immobilization of biopolymer such as proteins on organic polymer surfaces is a well known technique, and is fully described in the literature referred to above and below. The above description merely provides details for adaptation of the technique to the process of the present invention. All other aspects of the process conform with previously known parameters, as will be apparent to those skilled in this art.

Examples of suitable polyalkylene glycols are those in which ethylene oxide and alkylene oxides having from three to four carbon atoms, or tetrahydrofuran, are randomly distributed or distributed in blocks. Especially suitable are polyalkylene glycols having a molecular weight within the range from about 2,000 to about 10,000, and containing one or more blocks of polyoxypropylene and polyoxyethylene having a molecular weight within the range from about 300 to about 3,000. Other types of suitable polyalkylene glycols are adducts of ethylene oxide in combination with higher 3 to 4 carbon atom alkylene oxides, or tetrahydrofuran, with a dihydroxy or polyhydroxy compound, such as glycerol or pentaerythritol.

The cellulose ethers preferably have such a degree of polymerisation that a 1% aqueous solution thereof has a Brookfield viscosity within the range from about 10 to about 10,000 cP, preferably from about 30 to about 5,000 cP, measured at LV, 12 rpm, at 20° C. They may comprise hydrophobic hydrocarbon groups, such as methyl, ethyl, propyl, butyl, amyl, hexyl, heptyl, benzyl and higher hydrocarbon groups having from about 8 to about 24 carbon atoms, or polar hydroxyalkyl groups, such as hydroxyethyl, hydroxypropyl and hydroxybutyl, or mixtures of hydrocarbon groups and polar hydroxyalkyl groups. Examples of suitable cellulose ethers are methyl cellulose, ethyl cellulose, hydroxyethyl cellulose, hydroxypropyl cellulose, methyl hydroxyethyl cellulose, methyl hydroxypropyl cellulose, ethyl hydroxyethyl cellulose and benzyl ethyl hydroxyethyl cellulose. Alkyl hydroxyalkyl cellulose ethers are preferred.

To covalently bond the hydrophilic polymer to the carrier, and to covalently bond the protein to the hydrophilic polymer, reactive functional groups are introduced in conventional manner to serve as anchoring points. Examples of reactive groups that can be attached to the carrier are amino, carboxyl or hydroxyl groups, with which the hydrophilic nonionic polymer or an activated form thereof can react. The hydrophilic polymer preferably comprises reactive groups, such as epoxy, tresylate, carbonyl imidazole and acyl azide groups capable of reacting with reactive groups on the carrier and with the protein which is normally bonded via one or more of its amino, thiol and/or phenolic hydroxyl groups. This immobilization technique is well known to those skilled in this art, and is described in detail in inter alia, "Surface and Interfacial Aspects of Biomedical Polymers", Ed. J. D. Andrade, Plenum Press 1985, Vol. 2, p 81, and C. G. Golander: "Preparation and Properties of Functionalized Polymer Surfaces", Dissertation, Royal Institute of Technology, Stockholm 1986, which are hereby included by reference as part of this specification.

In the event that the protein is a glycoprotein, bonding may occur to the aldehyde groups generated in the carbohydrate moiety by oxidation with, for example, sodium periodate. It is also possible to anchor the hydrophilic polymer to the solid polymer surface in conventional manner by physical adsorption.

The following Examples represent preferred embodiments of the invention.

EXAMPLE 1

Carboxyl groups were formed on the surface of a 2 cm×2 cm polystyrene plate by plasma polymerisation of acrylic acid on the surface. The carboxyl-functional surface was then treated with a 10% solution of diaminopropane in water in the presence of water-soluble carbodiimide (0.6%) at pH 4.5-5.0. The plate was rinsed with distilled water, and treated with a 10% solution of a nonionic polymer, the diepoxide of a block copolymer of ethylene oxide and propylene oxide having a molecular weight of 2,000 and a cloud point of 40° C., at pH 9.5 for 15 hours at 20° C.

A 10% carbonate buffer of pH 9.5 and containing 0.5 mg/ml immunoglobulin G (IgG) was heated to 40° C. and contacted with these epoxy-functional plates. The reaction was allowed to proceed for 2 hours at 40° C.

As controls, use was made (Control (1)) of a polystyrene plate which had been hydrophilised in the same way as above, but in which the epoxide groups, before contact with the IgG solution at 40° C., had been removed by treatment with lye and, Control (2), a polystyrene plate which had been hydrophilised as above, but in which the treatment with the IgG solution was carried out at 20° C. instead of 40° C. In the latter case, the reaction time was 2 hours and, alternatively, in Control (3), 8 hours.

The amount of immobilised IgG was measured with enzyme-conjugated antibodies against IgG according to ELISA (see, for instance, A. Voller and D. E. Bidwell in "Alternative Immunoassays" (W. P. Collins, Ed.) Chap. 6, Wiley, N.Y. 1985). Evaluation was carried out by conventional spectroscopic technique.

| Sample | Amount of Immobilised IgG Adsorption at 495 mm |
| --- | --- |
| Control (1) Surface without epoxide groups, 2 hours | 0.167 |
| Control (2) Bonding at 20° C., 2 hours | 0.380 |
| Control (3) Bonding at 20° C., 8 hours | 0.405 |
| Example 1 Bonding at 40° C., 2 hours | 2.450 |

As is apparent from the results, the amount of immobilised immunoactive protein is vastly increased when the bonding temperature is at the cloud point, as compared with a temperature of 20° C. below this point. The increased immobilisation leads to improved sensitivity in immunodiagnostics.

EXAMPLES 2 AND 3

A 12 cm×8 cm PVC plate and intended to form part of an extracorporeal chamber, was grafted with crotonic acid under irradiation with UV light of wavelength 320 nm and in the presence of benzophenone as initiator. The resulting carboxyl-functional surface was treated with a 10% solution polyethylene imine in water in the presence of a water-soluble carbodiimide (0.6%) at pH 4.5-5.0. The plate was then treated with a 10% solution of the bis(carbonyl imidazole) derivative of a block copolymer of ethylene oxide and propylene oxide having a molecular weight of 4,000 and a cloud point of 38° C. at pH 8.0 for 3 hours at 20° C.

A 10% carbonate buffer of pH 8.0 and containing 50,000 U/ml γ-Interferon was contacted with the carbonyl imidazole-functional hydrophilised PVC plates, and the reaction was allowed to proceed for 2 hours and 8 hours at 20° C. (Controls (3) and (4)), 30° C. (Controls (5) and ((6)), and 40° C. (Examples 2 and 3).

Peripheral mononuclear blood cells were isolated by gradient centrifugation on Lymphoprep (Ficoll solution). The cells were diluted to $1 \cdot 10^6$/ml in the tissue culture medium RPMI 1640 with addition of 10% by weight of fetal calf serum (FCS) and 1% by weight of the antibiotic Penicillin streptomycin (PEST) and incubated on the γ-Interferon-immobilised plate for 7 days at 37° C. and 5% $CO_2$.

As Controls, use was also made of two plates, one of which (Control (1)) had only been hydrophilised as above, and, Control (2) hydrophilised as above and to which free γ-Interferon was added directly into the cell culture at the beginning of the incubation.

Neopterin was used as a marker for the cell stimulation obtained. It is well know that mononuclear blood cells such as lymphocytes and macrophages, secrete neopterin when stimulated by, inter alia, γ-Interferon.

| Sample | Neopterin (nmol/l) |
| --- | --- |
| Control (1) Hydrophilised surface without γ-Interferon | 5 |
| Control (2) Hydrophilised surface with free γ-Interferon added | 83 |
| Control (3) Bonding at 20° C., 2 hours | 9 |
| Control (4) Bonding at 20° C., 8 hours | 11 |
| Control (5) Bonding at 30° C., 2 hours | 15 |
| Control (6) Bonding at 30° C., 8 hours | 20 |
| Example 2 Bonding at 40° C., 2 hours | 60 |
| Example 3 Bonding at 40° C., 8 hours | 62 |

The results (Controls (3) to (5)) indicate that the biologically active γ-Interferon was immobilised to a far higher degree when the immobilisation was carried out in accordance with the invention (40° C.) than when carried out at lower temperature (20° and 30° C.). This circumstance may be utilised for cell stimulation, for example in extracorporeal therapy.

EXAMPLE 4

Silica (10 g) was reflux-boiled overnight in 150 ml of a 10% solution of 3-aminopropyl trimethoxy silane in toluene. The resulting aminopropyl silica was added to a solution consisting of 1 g periodate-oxidised ethyl hydroxyethyl cellulose having a cloud point of 42° C. in 40 g aqueous solution of pH 7 in the presence of 0.5 g sodium cyanoborohydride. The reaction was allowed to proceed at 22° C. under shaking for 16 hours. The silica was filtered off and carefully washed with water.

To the aldehyde-functional cellulose-treated silica a 30 g aqueous solution was added, consisting of 33 mg/ml lipase and 0.5 g sodium cyanoborohydride. The reaction was allowed to continue for 16 hours at pH 7, both at 20° C. (Control) and at 40° C. (Example 4). Then the particles were washed alternately with carbonate buffer, pH 9.0, and acetate buffer, pH 4.0.

The amount of bonded protein was determined at 35 mg/g silica for the reaction at 40° C., and at 4 mg/g silica for the reaction at 20° C. The activity of the lipase from the 40° C. reaction was measured in a transesterification reaction (incorporation of stearic acid in a triglyceride) and found to be 56% of the activity of free lipase. The same activity was found for lipase immobilised at 20° C., which means that the capacity of the preparation in accordance with the invention is about nine times higher than for the comparison preparation.

Having regard to the foregoing specification, the following is claimed as the inventive and patentable embodiments thereof:

1. A process for covalently bonding protein to a carrier surface coated with hydrophilic nonionic polymer having groups reactive with the protein and having a cloud point in the reaction medium that is at least 5° C. above the temperature at which the coated carrier surface is to be used, which comprises reacting protein with the hydrophilic nonionic polymer on the carrier surface in an aqueous reaction medium at a temperature not less than 5° C. below the cloud point but not above a temperature at which protein is deleteriously affected, thereby immobilizing protein on the surface by coupling protein thereto via protein-reactant groups of the nonionic polymer forming covalent bonds, and having low spontaneous adsorption of proteins through electrostatic attraction or hydrophobic interaction.

2. A process according to claim 1 in which the hydrophilic nonionic polymer has a cloud point within the range from about 30° to about 100° C.

3. A process according to claim 1 in which the hydrophilic nonionic polymer is a polyalkylene glycol.

4. A process according to claim 1 in which the hydrophilic nonionic polymer is a cellulose ether.

5. A process according to claim 4 in which the cellulose ether is an alkyl hydroxyalkyl cellulose having a Brookfield viscosity of within the range from about 30 to about 5,000 cP, measured at LV, 12 rpm at 20° C.

6. A process according to claim 4 in which hydrophilic nonionic cellulose ether has a cloud point at least 10° C. above the temperature at which the coated carrier surface is to be used.

7. A process according to claim 1 in which the hydrophilic nonionic polymer has at least one member selected from the group consisting of epoxy, tresylate, carbonyl imidazole and acyl azide groups capable of reacting with reactive groups of the protein.

8. A process according to claim 1 in which the maximum reaction temperature is about 100° C.

9. A process according to claim 1 in which the maximum reaction temperature is within the range from about 30° to about 50° C.

10. A process according to claim 1 in which the pH of the aqueous reaction medium is within the range from about 4 to about 9.

* * * * *